US011434194B2

(12) United States Patent
Lourenço et al.

(10) Patent No.: US 11,434,194 B2
(45) Date of Patent: Sep. 6, 2022

(54) AMORPHOUS FORM OF VILANTEROL TRIFENATATE AND PROCESSES FOR THE PREPARATION THEREOF

(71) Applicant: Hovione Scientia Limited, Cork (IE)

(72) Inventors: Nuno Torres Lourenço, Lisbon (PT); Luis Sobral, Montijo (PT); Joana Fernandes, Lançada (PT)

(73) Assignee: Hovione Scientia Limited, Cork (IE)

( * ) Notice: Subject to any disclaimer, the term of this patent is extended or adjusted under 35 U.S.C. 154(b) by 311 days.

(21) Appl. No.: 16/631,683

(22) PCT Filed: Jul. 9, 2018

(86) PCT No.: PCT/GB2018/051940
§ 371 (c)(1),
(2) Date: Jan. 16, 2020

(87) PCT Pub. No.: WO2019/016512
PCT Pub. Date: Jan. 24, 2019

(65) Prior Publication Data
US 2020/0165190 A1    May 28, 2020

(30) Foreign Application Priority Data

Jul. 19, 2017  (PT) .................................... 110209

(51) Int. Cl.
| | |
|---|---|
| *C07C 217/08* | (2006.01) |
| *A61P 11/06* | (2006.01) |
| *A61P 11/00* | (2006.01) |
| *A61K 31/138* | (2006.01) |
| *C07C 213/10* | (2006.01) |
| *C07C 215/60* | (2006.01) |

(52) U.S. Cl.
CPC .......... *C07C 217/08* (2013.01); *A61K 31/138* (2013.01); *A61P 11/00* (2018.01); *A61P 11/06* (2018.01); *C07C 213/10* (2013.01); *C07C 215/60* (2013.01); *C07B 2200/13* (2013.01)

(58) Field of Classification Search
None
See application file for complete search history.

(56) References Cited

FOREIGN PATENT DOCUMENTS

| | | |
|---|---|---|
| PT | 110209 | 7/2017 |
| WO | 03024439 A1 | 3/2003 |
| WO | 2003024439 A1 | 3/2003 |

(Continued)

OTHER PUBLICATIONS

Foreign communication from related application—International Search Report and Written Opinion of the International Searching Authority, Application No. PCT/GB2018/051940, dated Oct. 2, 2018, 10 pages.

(Continued)

*Primary Examiner* — Brian J Davis
(74) *Attorney, Agent, or Firm* — Conley Rose, P.C.; Rodney B. Carroll

(57) ABSTRACT

The present invention relates to an amorphous form of vilanterol trifenatate, processes for its preparation and its use in pharmaceutical formulations for the treatment of respiratory diseases, particularly for the treatment of asthma and chronic obstructive pulmonary disease. In particular, the invention relates to an amorphous form of vilanterol trifenatate, characterized by the X-ray powder diffraction (XRPD) pattern, obtained using copper K-alpha1 radiation.

19 Claims, 5 Drawing Sheets

(56) References Cited

FOREIGN PATENT DOCUMENTS

| | | |
|---|---|---|
| WO | 2014041565 A2 | 3/2014 |
| WO | 2017001907 A1 | 1/2017 |
| WO | 2019016512 A1 | 1/2019 |

OTHER PUBLICATIONS

Murikipudi, Vasudha et al., "Efficient throughput method for hygroscopicity classification of active and inactive pharmaceutical ingredients by water vapor sorption analysis", Pharmaceutical Development and Technology, 2013, pp. 348-358, vol. 18, No. 2, Informa Healthcare USA, Inc.

Procopiou, Panayiotis A. et al., "Synthesis and Structure Activity Relationships of Long-acting β2 Adrenergic Receptor Agonists Incorporating Metabolic Inactivation: An Antedrug Approach", Journal of Medicinal Chemistry, 2010, pp. 4522-4530, vol. 53, American Chemical Society.

"604002 Crystalline forms of Vilanterol base and vilanterol trifenatate". Research Disclosure, Aug. 2014, pp. 772-773, vol. 604, The British Library.

Foreign communication from related application—International Preliminary Reporton Patentability, Application No. PCT/GB2018/051940, dated Oct. 14, 2019, 8 pages.

Foreign communication from a related application—Examination Report of Indian Patent Application No. 202017004652, dated Jul. 1, 2021, 4 pages.

Chemistry Reviews of NDA 203975, Application No. 203975Orig1s000, Center for Drug Evaluation and Research, 2013, 55 pages.

AMORPHOUS FORM OF VILANTEROL TRIFENATATE AND PROCESSES FOR THE PREPARATION THEREOF

CROSS REFERENCE TO RELATED APPLICATIONS

This application is a filing under 35 U.S.C. 371 of International Application No. PCT/GB2018/051940 filed Jul. 9, 2018, entitled "Amorphous Form of Vilanterol Trifenatate and Processes for the Preparation Thereof," which claims priority to Portuguese Patent Application No. 110209 filed Jul. 19, 2017, which applications are incorporated by reference herein in their entirety.

DESCRIPTION

The present invention relates to an amorphous form of vilanterol trifenatate, processes for its preparation and its use in pharmaceutical formulations for the treatment of respiratory diseases, particularly for the treatment of asthma and chronic obstructive pulmonary disease.

BACKGROUND

The compound vilanterol trifenatate, of molecular structure (I) depicted below, is used (typically via inhalation) as a long-acting beta$_2$-agonist (LABA) for the treatment of respiratory diseases such as, bronchial asthma and chronic obstructive pulmonary disease.

(I)

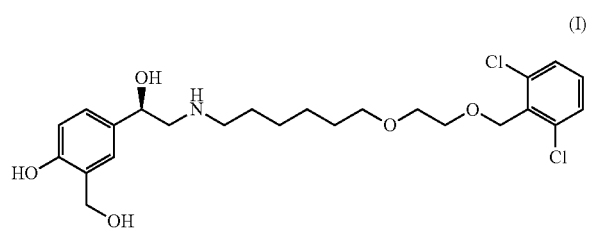

-continued

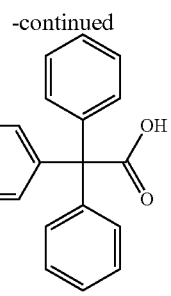

Vilanterol trifenatate, designated by 4-((1R)-2-((6-(2-((2,6-Dichlorophenyl)methoxy)ethoxy)-hexyl)amino)-1-hydroxyethyl)-2-(hydroxymethyl)phenol triphenylacetate, was first claimed by Glaxo (now GlaxoSmithKline (GSK)) in WO 2003/024439 as optically pure (R)-isomer in the form of the trifenatate salt. For further reference, we designate herein the form described in WO 2003/024439 as crystalline vilanterol trifenatate, or simply vilanterol trifenatate. Vilanterol trifenatate is preferably administered by inhalation, in fixed combination with fluticasone propionate, using the inhaler Breo Ellipta® that delivers powdered vilanterol/fluticasone from foil-wrapped blisters. It is also administered by inhalation in fixed combination with umeclidinium bromide using the inhaler Anoro Ellipta® that delivers powdered vilanterol/umeclidinium from foil-wrapped blisters. GSK is currently developing a once-daily 'closed' triple therapy of an inhaled corticosteroid/long-acting beta-2-agonists/long-acting muscarinic antagonist combination (Fluticasone Furoate/Umeclidinium Bromide/Vilanterol Trifenatate) in a single device, with the aim of providing a new treatment option for the management of asthma by improving lung function, health-related quality of life and symptom control over established combination therapies (ClinicalTrials.gov; Identifier: NCT03184987).

Crystalline vilanterol, as well as certain acceptable salts thereof, and processes for the preparation thereof, are described in WO 2003/024439 and in J. Med. Chem. 2010, 53 (4522-4530), authored by GSK scientists. The reaction sequence is schematically represented as follows, in which it is shown that ethanol is used as the solvent at 80° C. in the conversion of the vilanterol base to the trifenatate salt:

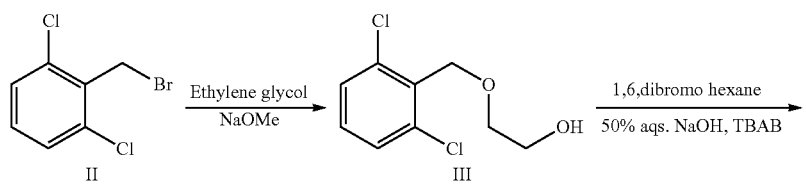

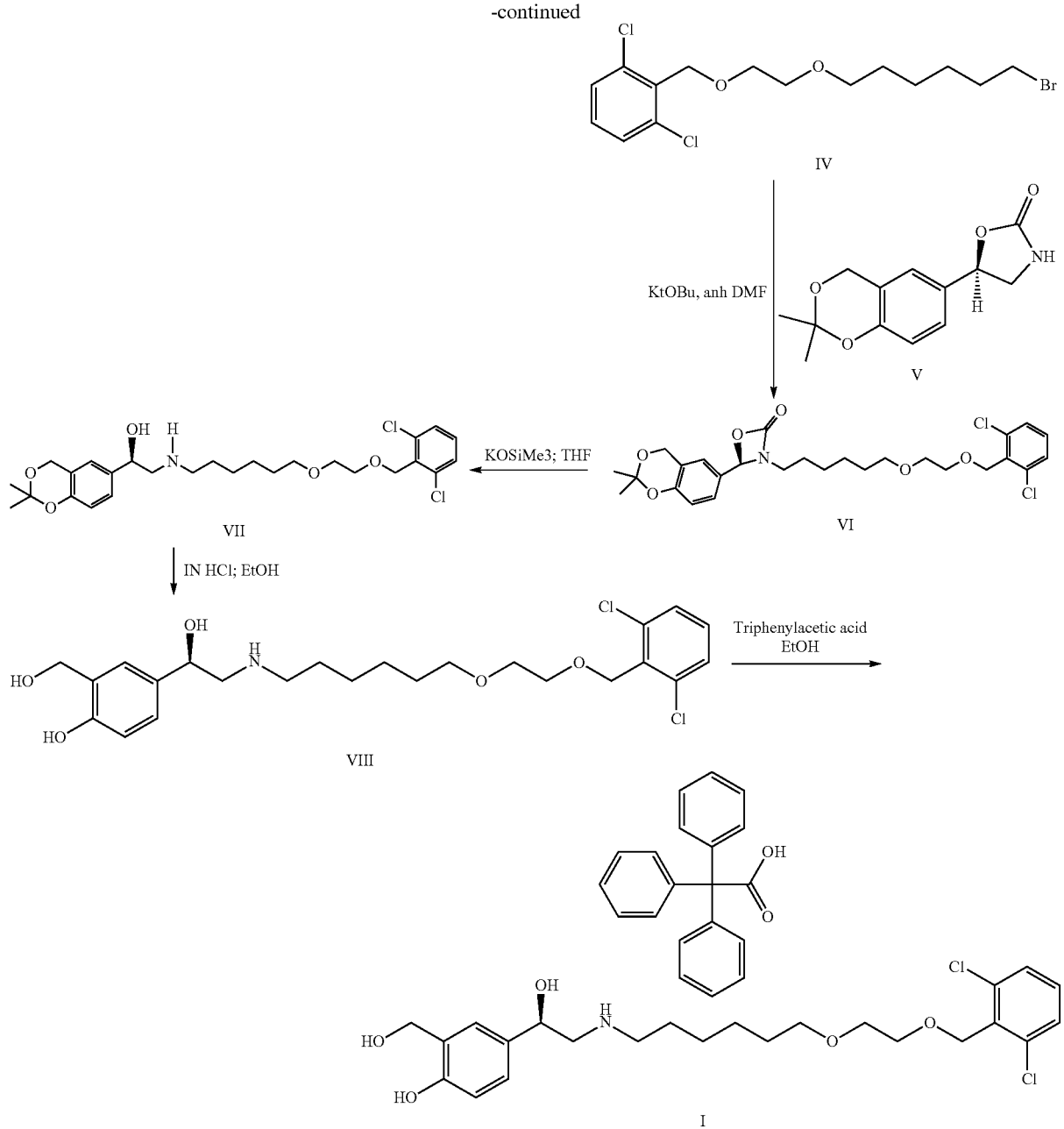

No analysis with respect to the crystal formed is disclosed in either of these documents. Also, no isolation and identification/characterisation of any other forms, crystalline or amorphous, of vilanterol trifenatate is disclosed in either of these documents.

Given the interest in the drug, other companies have experimented with various aspects, including *Laurus* Labs, who in patent specification no. WO 2014/041565 report attempting to prepare crystalline vilanterol trifenatate using the process disclosed in the GSK specification referred to above, which resulted in a higher than desired level of impurity. They tried performing reactions in alcoholic solvents such as methanol and isopropanol, but noted that these did not result in exceptional yields or purity. Instead, they teach using a non-alcoholic solvent, preferably acetone, which results in a crystalline product having a decreased impurity profile (greater than 99.5% purity by HPLC; no single impurity greater than 0.1%); no indication is given that these reactions produced an amorphous product. No indication is given by *Laurus* Labs that the trifenatate salt prepared by their method is other than the same as that described by GSK.

An anonymous research disclosure appeared in a publication of Industrial Opportunities Ltd, vol 604(2), pp 772-774 (August 2014) concerning '*Crystalline forms of vilanterol base and vilanterol trifenatate*'. This research disclosure tabulates five hydrates or solvates of vilanterol trifenatate and three anhydrous forms, together with an alleged 'amorphous' form. Scant details are provided regarding their preparation from the GSK vilanterol trifenatate crystal referred to above (also referred to in the research disclosure as 'Form I')). The research disclosure lists XPRD peaks of Form I and each of their 8 crystalline forms, and an XRPD graph is provided for two of these alleged crystalline forms. No further characterization is provided, including for the alleged amorphous form.

However, these data are called into question, not least because, when repeating the method described in the research disclosure for the preparation of the form designated therein as 'amorphous': not only did present inventors find that the product was, in fact, crystalline and substantially indistinguishable (by XPRD) from the original form I of GSK, as shown in comparative example 1 and FIG. 6b, herein below, but they also found that this form prepared according to the research disclosure has an identical melting point (134° C.) as to that of Form I (cf. FIG. 7). Accordingly, the research disclosure is insufficient and/or inaccurate in its description and/or characterization of the amorphous form allegedly isolated.

Furthermore, no data are provided in the research disclosure that would indicate that any of the forms prepared therein would provide a credible, amorphous alternative for potential use in medicine.

A few years later, Teva described in WO 2017/001907 a biocatalytic process for the preparation of crystalline vilanterol. Additionally, they disclose the preparation of vilanterol in the form of the L-tartrate salt, which can then be converted in a multi-step process via the base (by addition of the corresponding acid) to the crystalline trifenatate salt (99.8% pure). Again, no indication is given by Teva that the trifenatate salt prepared by their method is other than the same as that described by GSK, and no amorphous form is prepared.

The uncertainties about the molecular rearrangement of vilanterol trifenatate disclosed in these prior art documents moved the present inventors to develop methods to prepare and identify a new form of vilanterol trifenatate.

Some molecular rearrangements of active pharmaceutical ingredients (APIs) often have disadvantageous properties. These properties depend on the solid state and can be modified by changing the solid forms, typically forms such as different polymorphs, solvates, hydrates, salts and co-crystals. In particular, drugs for the treatment of respiratory diseases are frequently administered via dry powder inhalation devices. Formulating respiratory drugs as dry powders with inhalation excipients is not a straightforward process. The use of APIs with differentiated properties allows a better preparation of dry powder formulations with proper (desired) bioavailability and physical properties. Bioavailability and physical characteristics are important for an efficient administration of the drug substance, to ensure that an effective dose is delivered to the correct part of the lung and that the drug is effective in treating respiratory diseases.

As is apparent from the above summary of the prior art, no non-crystalline forms of vilanterol trifenatate are known in the prior art, let alone sufficiently and/or accurately described and/or characterised.

DETAILED DESCRIPTION OF THE INVENTION

Amorphous Form and Characterization Thereof

Crystalline forms of active pharmaceutical ingredients are often preferred over non-crystalline forms due to their better stability and purity. As such, when looking for new forms of a compound, in particular when a commercially available crystal form already exists, it is customary to investigate further crystal forms of the compound which may have different properties or characteristics. Generally, one does not seek to provide a non-crystalline form, at least for the reasons described herein.

Contrary to the efforts of others in this field, the present inventors have isolated and identified/characterised, for the first time, an amorphous form of vilanterol trifenatate, which may be used as an alternative to Form I in a pharmaceutical formulation.

The present inventors have found an amorphous form of vilanterol trifenatate which, surprisingly, has comparable stability properties with respect to Form I.

Accordingly, there is provided by the present invention an amorphous form of vilanterol trifenatate. The amorphous form of vilanterol trifenatate, described herein, may be characterised by the X-ray powder diffraction (XRPD) pattern obtained using copper K-alpha1 radiation depicted in FIG. 1.

In another aspect of the present invention, there is provided an amorphous form of vilanterol trifenatate obtained by spray drying a solution comprising vilanterol trifenatate.

In accordance with any aspect of the present invention, the amorphous form of vilanterol trifenatate, described herein, may be characterised, or further characterised, by any one or more physical properties based on physical measurements and analyses conducted thereon, as described herein.

In particular, in accordance with any aspect of the present invention, the amorphous form of vilanterol trifenatate may be characterised, or further characterised, by a differential scanning calorimetry (DSC) profile having a glass transition (Tg) event at 32° C. and a degradation event with an onset at 189° C. and a peak at 191° C., wherein the differential scanning calorimetry measurement is performed in accordance with the methods and parameters described herein.

Figure 3:
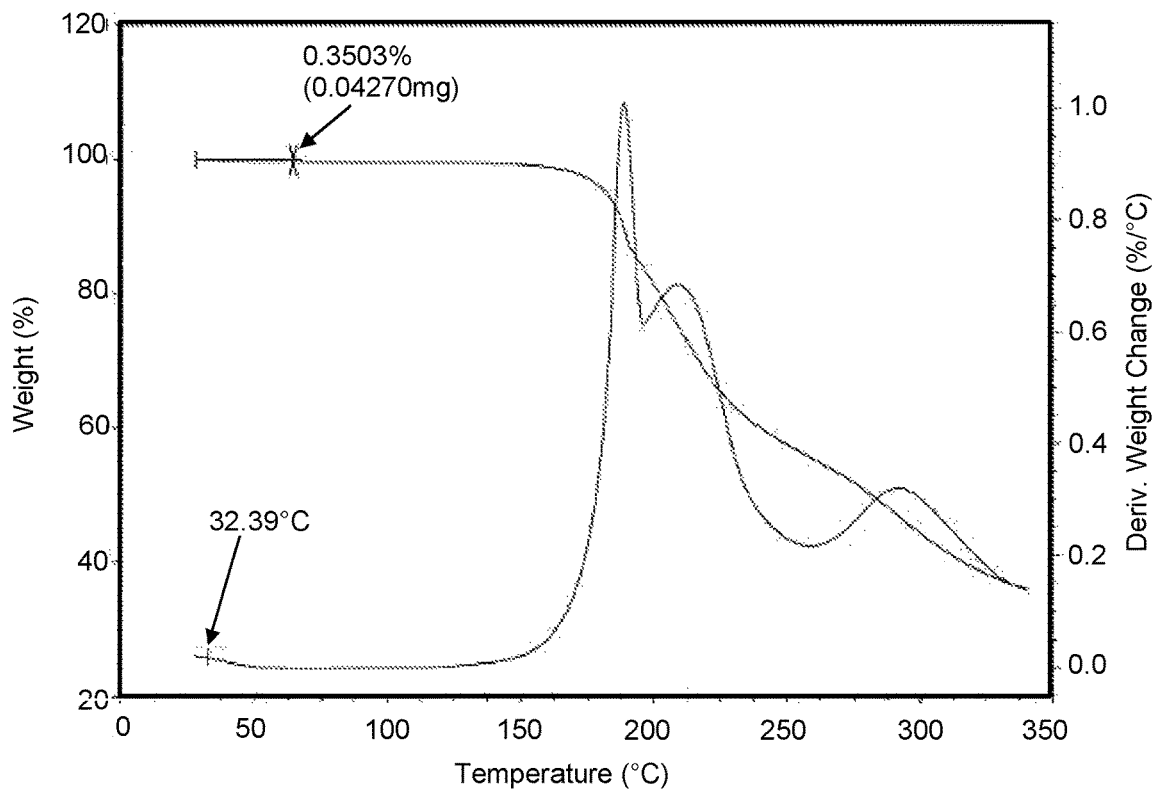
FIG. 3: TGA profile of the amorphous form of vilanterol trifenatate.

In accordance with any aspect of the present invention, the amorphous form of vilanterol trifenatate may be characterised by a thermogravimetric analysis (TGA) profile having a weight loss of less than about 0.5%, preferably less than about 0.4%, and more preferably about 0.35% or less, as depicted in FIG. 3, wherein the thermogravimetric analysis is performed in accordance with the methods and parameters described herein.

Further, in accordance with any aspect of the present invention, the amorphous form of vilanterol trifenatate may be characterised by dynamic vapour sorption analysis showing a mass increase of less than about 2% at 80% RH at 25° C. preferably less than about 1.5% at 80% RH at 25° C., and most preferably less than about 1.4% at 80% RH at 25° C., wherein the dynamic vapour sorption analysis is performed in accordance with the methods and parameters described herein.

The result of the kinetic moisture sorption measurements are tabulated in Table 1. The values in the table are weight % variations that result from the use of the European Pharmacopoeia equation provided below. The hygroscopicity value is indicated from the sorption row at 80% RH of cycle 1. The table shows that the amorphous form of vilanterol trifenatate has a dynamic vapour sorption analysis showing a mass increase of 1.34% at 80% RH at 25° C.

TABLE 1

Dynamic vapour sorption analysis of amorphous vilanterol trifenatate.

| | | Change In Mass (%) | | |
|---|---|---|---|---|
| | Target RM (%) | Sorption | Desorption | Hysteresis |
| Cycle 1 | 0.0 | — | 1.186 | — |
| | 10.0 | — | 1.224 | — |
| | 20.0 | — | 1.257 | — |
| | 30.0 | — | 1.298 | — |
| | 40.0 | 0.001 | 1.333 | 1.332 |
| | 50.0 | 0.267 | 1.368 | 1.101 |
| | 60.0 | 0.618 | 1.401 | 0.784 |
| | 70.0 | 1.013 | 1.437 | 0.423 |
| | 80.0 | 1.344 | 1.474 | 0.131 |
| | 90.0 | 1.516 | 1.516 | — |
| Cycle 2 | 0.0 | 1.186 | 1.063 | — |
| | 10.0 | 1.180 | 1.186 | 0.006 |
| | 20.0 | 1.179 | 1.214 | 0.035 |
| | 30.0 | 1.182 | 1.243 | 0.061 |
| | 40.0 | 1.189 | 1.269 | 0.079 |
| | 50.0 | 1.205 | 1.294 | 0.090 |
| | 60.0 | 1.228 | 1.320 | 0.093 |
| | 70.0 | 1.262 | 1.345 | 0.084 |
| | 80.0 | 1.308 | 1.369 | 0.061 |
| | 90.0 | 1.393 | 1.393 | — |

In accordance with any aspect of the present invention, the amorphous form of vilanterol trifenatate may be characterised, or further characterised, as slightly hygroscopic based on results obtained by kinetic moisture sorption measurements obtained from dynamic vapour sorption analysis, and determining a % weight change using the following equation:

(1) % weight change=$[(W_2-W_1)/W_1]*100$, wherein $W_1$ is the weight of the sample at the start of the experiment at 25° C. and 40% RH, and $W_2$ is the weight of the sample at 25° C. and 80% RH in the first absorption cycle, and wherein, in accordance with the classifications of the version 7 of the European Pharmacopeia, a calculated weight change of 0.2-2% is indicative of a slightly hygroscopic substance.

Hygroscopicity describes the water uptake by a compound when under differing conditions of humidity. The more hygroscopic the compound, the higher the difference in the water content at different relative humidities. Active pharmaceutical ingredients (APIs) that change water content during formulation processes and in the final formulation need to be handled with more care with regard to environmental control during production and packaging. Accordingly, lower levels of hygroscopicity are advantageous.

Amorphous forms of compounds typically do not have a desirable level of stability in typical storage conditions (e.g. room temperature) relative to their corresponding crystalline form(s). This is because the amorphous form is often driven to the crystalline form (i.e. the thermodynamically stable form). As such, over time an amorphous compound will typically be expected to rearrange itself into a more (thermodynamically) stable crystal form. This not desirable in the pharmaceutical field; as a change in the physical structure of an active pharmaceutical ingredient causes a change in the physical properties thereof, such as dissolution rates.

Further, amorphous forms of biologically active drugs lack long-range order/structure, which typically results in reduced intermolecular bonding forces, which in turn makes such forms more susceptible to moisture (i.e. dissolution). This can cause phase changes of the active pharmaceutical ingredient, which reduces the efficacy of a dose, rendering it less stable than its crystal form.

Figure 4:
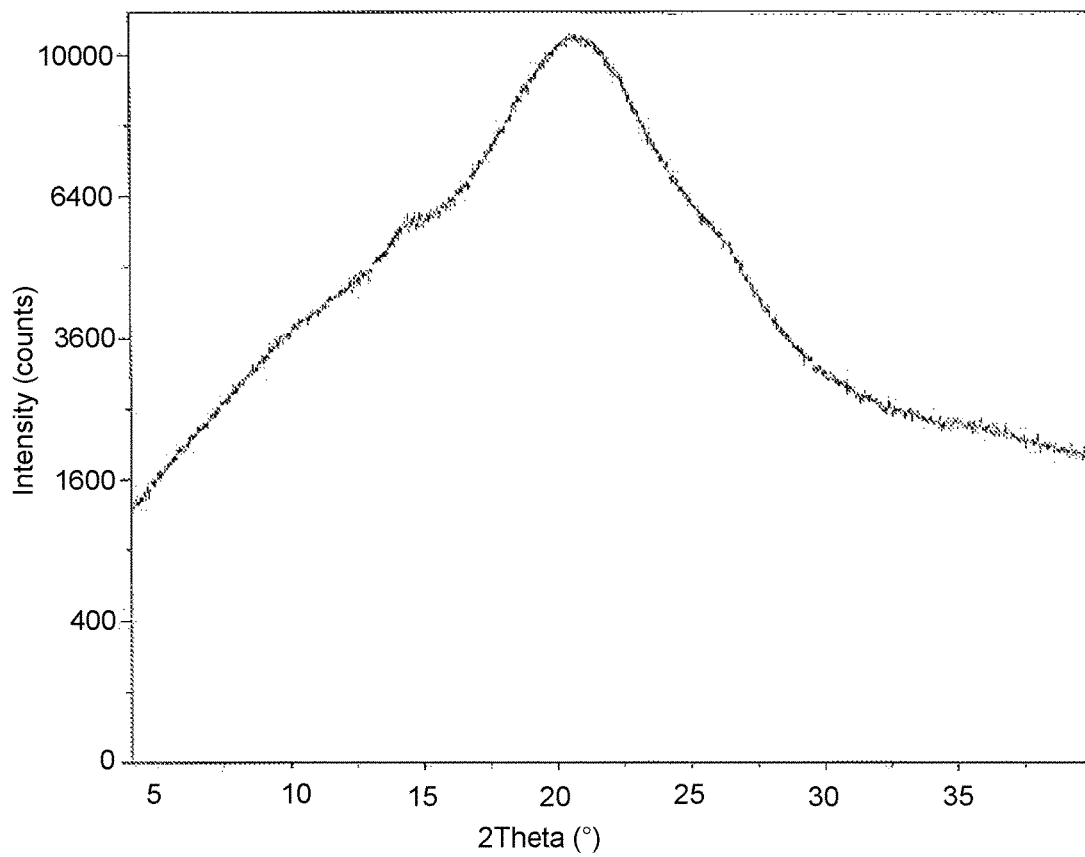
FIG. 4: XRPD diffractogram of the amorphous form of vilanterol trifenatate stored at room temperature for 5 months.
Figure 5A:
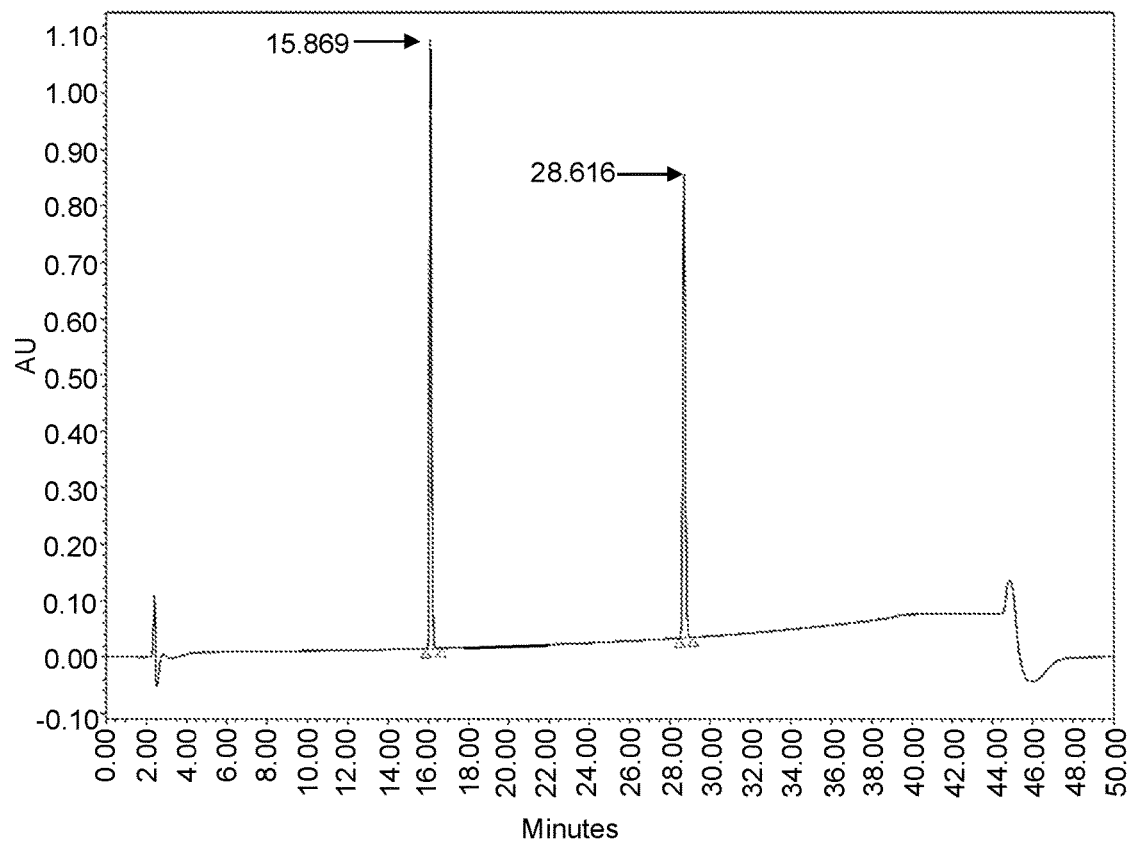
FIG. 5a: HPLC chromatogram of the amorphous form of vilanterol trifenatate.
Figure 5B:
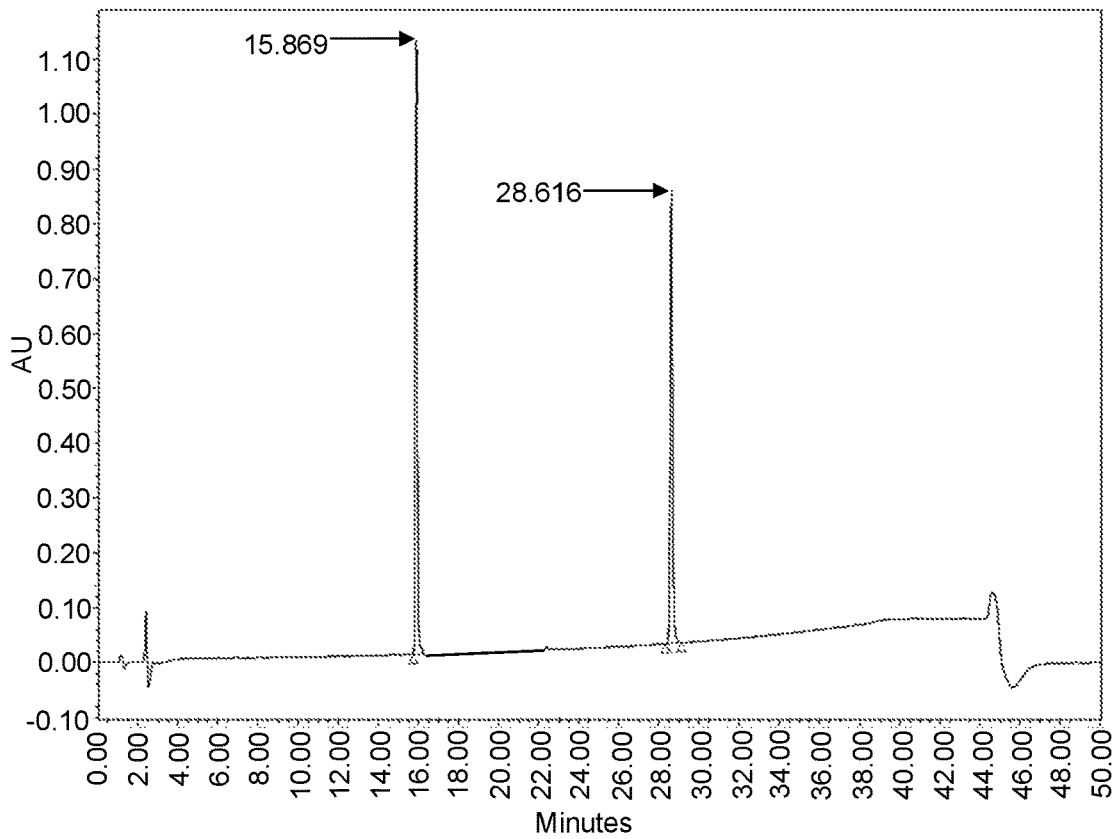
FIG. 5b: HPLC chromatogram of the amorphous form of vilanterol trifenatate stored at room temperature for 5 months.

However, surprisingly, the present inventors have found that the amorphous form of vilanterol trifenatate described herein is stable. This is demonstrated by the unchanged XRPD patterns of the amorphous form of vilanterol trifenatate from before and after exposure to conditions of 60% RH at 25° C. Such conditions reflect conditions similar to those in which the current medicaments (mentioned above) may be stored. Unexpectedly, the amorphous form of vilanterol trifenatate has also been shown to be stable at room temperature for long periods (at least 5 months). XRPD patterns and HPLC chromatograms of the amorphous form taken after storage at room temperature for at least 5 months showed that the amorphous form was stable, as the XRPD pattern and HPLC chromatograms remained the same (cf. FIG. 1 and FIG. 4, and see FIG. 5), i.e. no significant modifications in the XRPD pattern or in HPLC profile can be observed, as depicted in FIGS. 4, 5a and 5b, indicating an excellent stability. These results are at least as good as those measured for crystalline vilanterol trifenatate (i.e. Form I).

Accordingly, the amorphous form of vilanterol trifenatate may be characterised by XRPD patterns that are the same or substantially the same following exposure of the amorphous form of vilanterol trifenatate to conditions of 60% RH at 25° C. for 7 days.

In accordance with any aspect of the invention, the amorphous form of vilanterol trifenatate may be characterised by XRPD patterns that are the same or substantially the same following storage of the amorphous form of vilanterol trifenatate at room temperature for at least 5 months. In accordance with any aspect of the invention, the amorphous form of vilanterol trifenatate may be characterised by HPLC chromatograms that are the same or substantially the same following storage of the amorphous form of vilanterol trifenatate at room temperature for at least 5 months.

Visual solubility of the amorphous form of the invention in differing solvents was assessed according to the procedure described in the European Pharmacopeia 6.0 section 5.11. p. 659 (see corresponding SI dissolution ranges in Table 2), and compared with that for Form 1. The following method was used:

Dissolving procedure: the compound was shaken vigorously for 1 min and placed in a constant temperature device for 15 min at 25.0±0.5° C. If the compound was not completely dissolved, the shaking was repeated for 1 min and the tube placed in a constant temperature device for 15 min.

Method: 50 mg of compound was weighed in a stoppered tube, 0.05 mL of the solvent added and the Dissolving Procedure (see above) followed. If the compound was completely dissolved, it was defined very soluble.

If the compound was not completely dissolved, a further 0.45 mL of the solvent was added and the Dissolving Procedure (see above) followed. If the compound was completely dissolved, it was defined as freely soluble.

If the compound was still not completely dissolved, still further 1.0 mL of the solvent was added and the Dissolving Procedure (see above) followed. If the compound was completely dissolved, it was defined as soluble.

If the compound was still not completely dissolved, another 3.5 mL of the solvent was added and the Dissolving Procedure (see above) followed. If the compound was completely dissolved, it was defined as sparingly soluble.

If the compound was still not completely dissolved, the compound was slightly soluble or very slightly soluble. In this case, the suspension was heated up to the boiling point (max 80° C.) under stirring to verify the solubility at high temperature. The hot solution was afterwards cooled to room temperature to observe whether the compound precipitates. If the compound at room, temperature was completely dissolved, it is soluble at high temperature.

TABLE 2

Solubility ranges

| Descriptive terms | Abbreviation | Parts of solvent needed for 1 part solute | Solubility (mg/mL) |
|---|---|---|---|
| Very soluble | vs | <1 | >1000 |
| Freely soluble | FS | 1-10 | 100-1000 |
| Soluble | S | 10-30 | 33-100 |
| Sparingly soluble | SS | 30-100 | 10-33 |
| Slightly soluble | VSS | 100-1000 | 1-10 |
| Very slightly soluble | | 1000-10000 | 1-0.1 |
| Insoluble | INS | >10000 | <0.1 |

Results:

Form I and amorphous of vilanterol trifenatate are soluble in methanol at 25° C.

Form I is sparingly soluble in ethanol at 25° C.; amorphous vilanterol trifenatate is sparingly soluble in ethanol at 50° C.

Form I and amorphous of vilanterol trifenatate are freely soluble in THF at 25° C.

Form I of vilanterol trifenatate is freely soluble in 1,4-dioxane at 25° C.; amorphous of vilanterol trifenatate is soluble in 1,4-dioxane at 25° C.

Form I and amorphous of vilanterol trifenatate are insoluble in water at 75° C.

Surprisingly, the present inventors have found that the amorphous form of vilanterol trifenatate presents favourable physical properties such as, comparable stability and solubility with respect to crystalline Form I. Therefore, the amorphous form of vilanterol trifenatate described herein, surprisingly provides an alternative to the crystalline form of vilanterol trifenatate which is commercially available.

Pharmaceutical Formulations

In a further aspect of the present invention, there is provided a pharmaceutical formulation comprising: an amorphous form of vilanterol trifenatate in the pharmaceutical formulation characterised as described herein, and optionally one or more a pharmaceutically acceptable carriers therefor.

In accordance with any aspect of the present invention, any amorphous form of vilanterol trifenatate referred to herein, including that in the pharmaceutical formulation, may be characterised, or further characterised, as described herein.

Figure 1:
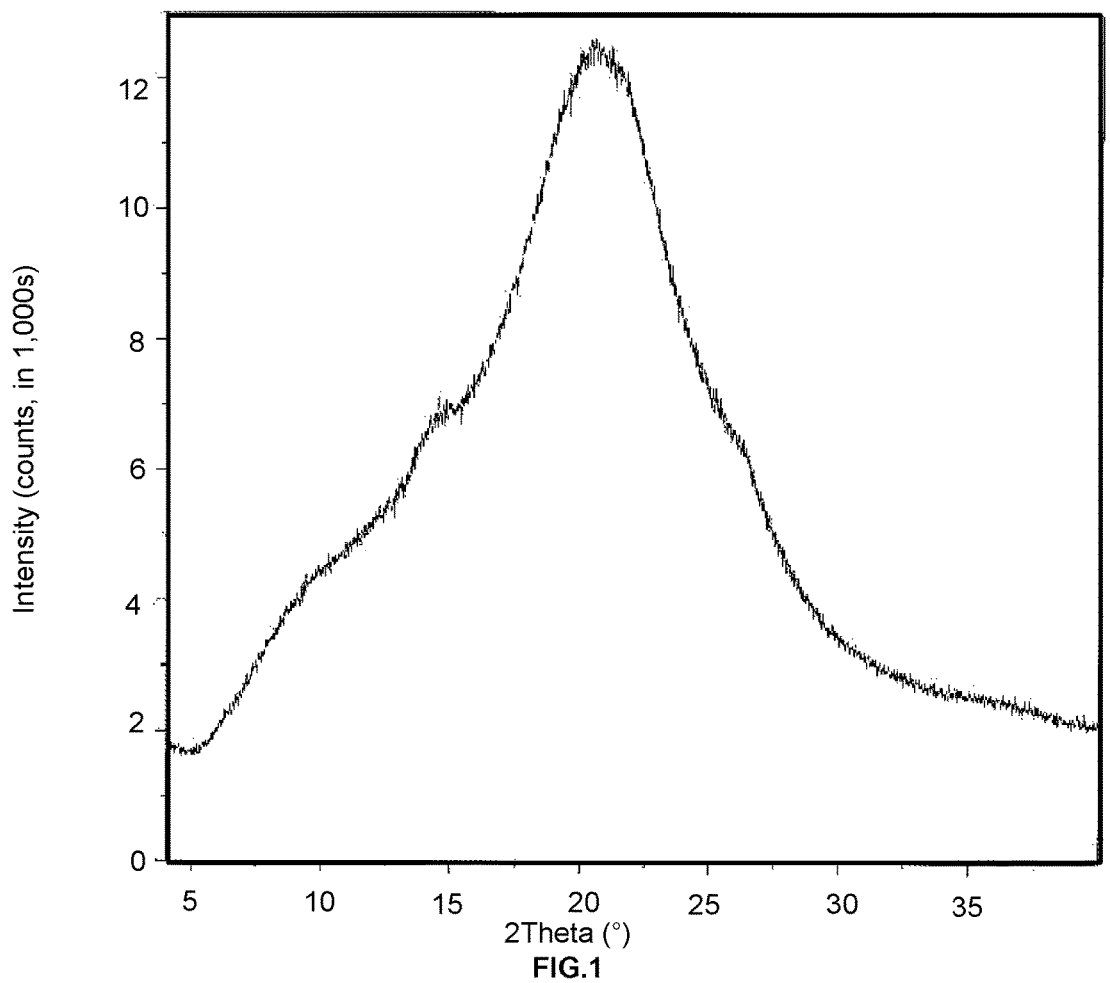
FIG. 1: XRPD diffractogram of the amorphous form of vilanterol trifenatate.
Figure 2:
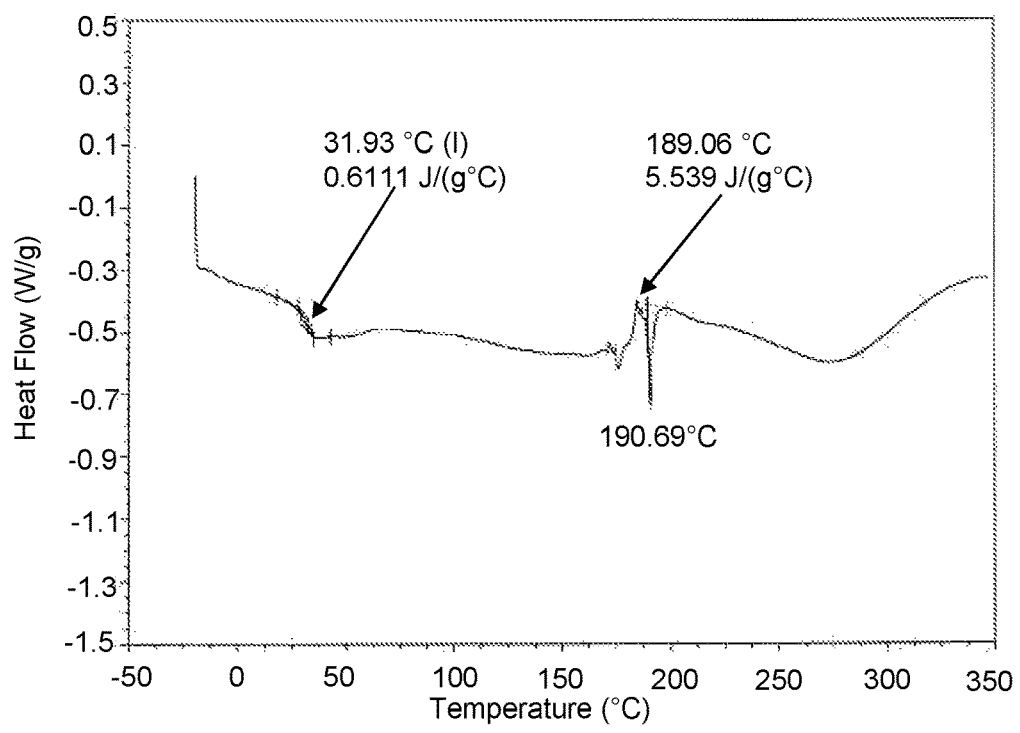
FIG. 2: DSC profile of the amorphous form of vilanterol trifenatate.

In particular, in accordance with any aspect of the present invention, the amorphous form of vilanterol trifenatate in the pharmaceutical formulation may be characterised by the X-ray powder diffraction (XRPD) pattern obtained using copper K-alpha1 radiation depicted in FIG. 1.

In accordance with any aspect of the present invention, the amorphous form of vilanterol trifenatate in the pharmaceutical formulation may be characterised, or further characterised, according to one or more of the following:

a differential scanning calorimetry profile having a glass transition (Tg) event at 32° C. and a degradation event with an onset at 189° C. and a peak at 191° C., wherein the differential scanning calorimetry measurement is performed in accordance with the methods and parameters described herein a thermogravimetric analysis (TGA) profile having a weight loss of less than about 0.5%, preferably less than about 0.4%, and more preferably 0.35% or less, as depicted in FIG. 3, wherein the thermogravimetric analysis is performed in accordance with the methods and parameters described herein dynamic vapour sorption (DVS) analysis showing a mass increase of less than about 2% at 80% RH at 25° C., preferably less than about 1.5% at 80% RH at 25° C., and most preferably less than about 1.4% at 80% RH at 25° C., wherein the dynamic vapour sorption analysis is performed in accordance with the methods and parameters described herein as slightly hygroscopic based on results obtained from kinetic moisture sorption measurements obtained by dynamic vapour sorption analysis, and determining a % weight change using the following equation:

(1) % weight change=$[(W_2-W_1)/W_1]*100$, wherein $W_1$ is the weight of the sample at the tart of the experiment at 25° C. and 40% RH and $W_2$ is the weight of the sample at 25° C. and 80% RH in the first absorption cycle, and wherein, in accordance with the classifications of the version 7 of the European Pharmacopeia, a calculated weight change of 0.2-2% is indicative of a slightly hygroscopic substance XRPD patterns that are the same or substantially the same following exposure of the amorphous form of vilanterol trifenatate to conditions of 60% RH at 25° C. for 7 days Accordingly, the invention further provides the use of an amorphous form of vilanterol trifenatate, as described herein, or pharmaceutical formulation thereof, in treating respiratory diseases, such as, and preferably, asthma and/or a chronic obstructive pulmonary disease.

A further aspect the present invention provides a method for treating respiratory diseases, such as asthma or a chronic obstructive pulmonary disease, wherein the method comprises administration of an effective amount of the amorphous form of vilanterol trifenatate, as defined herein, or a pharmaceutical formulation thereof, as described herein, to a patient in need thereof.

Further still, the present invention provides the amorphous form of vilanterol trifenatate, as defined herein, for use in the preparation of a medicament, particularly wherein the medicament is for use in treating respiratory diseases, such as, and preferably, asthma and/or a chronic obstructive pulmonary disease.

Respiratory diseases may include, but are not limited to, chronic obstructive pulmonary diseases like emphysema and chronic bronchitis; and refractory (non-reversible) asthma. In accordance with any aspect of the present invention, use of the amorphous form of vilanterol trifenatate may comprise administration thereof to a patient in need thereof, preferably in the form of a pharmaceutical formulation suitable for administration to the patient.

The pharmaceutical formulations of the present invention may be presented in any form known in the art of pharmacy and suitable for the API(s) and their purpose. In particular, such formulations may be suitable for inhalation, such as in powdered form, deliverable from foil-wrapped blisters. More preferably, the formulations of the present invention are in the form of micronized powders, having a particle size suitable for inhalation, preferably having a Dv90 less than 10 microns, as described further herein below.

Especially preferred is when the formulations of the present invention are provided in association with instructions for use thereof, optionally including dosage information, dosing regimen instructions and the like. Conveniently, the formulations of the present invention, together with any medical device such as inhalers (e.g. a dry powder inhaler), are packaged together in outer packaging which may include a carton, box or other suitable container for the composition and instructions (i.e. as a kit).

Accordingly, amorphous vilanterol trifenatate obtained or characterised according to any aspect of the present invention may be micronized, for example to obtain a particle size, or particle size distribution, suitable for inhalation, such as buccal inhalation. For use in accordance with any aspect of the invention, there is described herein a micronization process to tailor the particle size of the amorphous form of vilanterol trifenatate. The process does not alter the structure or phase of the amorphous form. The process involves feeding the amorphous form into a fluid energy jet mill. In practice, the conditions of such a micronization process may be adjusted, as known by those skilled in the art, to provide the desired particle size/size distribution. In particular, the particles to be micronized may be fed into a fluid energy jet mill at flow rate suitable to achieve the desired degree of micronization. For example, the flow rate may be, at least about 1 g/h, or at least about 10 g/h, or preferably at least between about 5-200 g/h, or more preferably between about 10-100 g/h or about 18-90 g/h. The fluid energy jet mill may be operated with, for example $N_2$ gas, and be operated at a suitable pressure, for example at a pressure of 1-10 bar for the venturi and a pressure of 1-10 bar for the ring.

For use in accordance with any aspect of the invention, the amorphous form of vilanterol trifenatate may have a particle size of less than or about 12 μm, preferably less than or about 10 μm, e.g. below about 5 μm, such as in a range between about 2-10, 3-9 or 4-8 μm.

For use in accordance with any aspect of the invention, the amorphous form of vilanterol trifenatate may have a particle size distribution wherein the Dv50 is less than or about 12 μm, preferably less than or about 10 μm, and most preferably in a range between about 2-10, 3-9 or 4-8 μm.

For use in accordance with any aspect of the invention, the amorphous form of vilanterol trifenatate may have a particle size distribution wherein the Dv90 is less than or about 12 μm, preferably less than or about 10 μm, and most preferably in a range between about 2-10, 3-9 or 4-8 μm.

In accordance with any aspect of the present invention, the pharmaceutical formulations may further comprise one or more additional active pharmaceutical ingredients (API).

Additional active pharmaceutical ingredients may include any biologically active agents, preferably those which may be used to treat respiratory diseases, or facilitate such treatment. Additional active pharmaceutical ingredient(s) may include, but are not limited to, one or more of long-acting beta$_2$-agonists (LABA), corticosteroids, long-acting muscarinic antagonists and short-acting beta$_2$-adrenergic agonists. Preferably, the additional active ingredients comprise one or more of fluticasone furoate and umeclidinium bromide. The additional API(s) may be comprised in any pharmaceutically formulation referred to herein.

For use in accordance with any aspect of the present invention, the additional active pharmaceutical ingredient (s), or in particular the pharmaceutical formulation comprising the additional active pharmaceutical ingredient(s), may be administered at any suitable pharmacological dose, it being understood that the exact amounts (i.e. the therapeutically effective amount) will depend upon the nature of each of the APIs (including any additional APIs) and the condition to be treated. For example, suitable doses for each (independently) or all the APIs may comprise a daily dosage of from about 0.001 milligram (i.e. 1 microgram) to about 100 milligrams per day, optionally given as a single daily dose or in divided doses two to six times a day, or in sustained release form.

The one or more pharmaceutically acceptable carriers for each API may be the same or different. In accordance with any one of the aspects of the present invention described herein, the amorphous form of vilanterol trifenatate, and the one or more additional active pharmaceutical ingredient(s) may be for administration separately, sequentially or simultaneously.

Although the preferred formulations of the present invention are in a form suitable for administration by inhalation, more preferably buccal inhalation, the pharmaceutical formulations of any aspect of this invention may include compositions suitable for oral, rectal, topical, parenteral, including subcutaneous, intramuscular, and intravenous, ocular (ophthalmic), pulmonary (nasal or buccal inhalation), or nasal administration (such as, for example, in the form of liquid drops or spray), although the most suitable route in any given case will depend on the nature and severity of the conditions being treated and on the nature (e.g. particle size) of the API, and where appropriate the additional active ingredients present.

The pharmaceutical formulation may be conveniently presented in unit dosage form (e.g. a fixed dosage form) and formulated by any of the methods well-known in the art of pharmacy. Inhalation dosage forms, such as buccal inhalation, represent an advantageous dosage form as they allow fast delivery of an effective amount to a target area (i.e. the airways and lungs) whilst minimizing systemic exposure, as such, they may be preferred.

In practice, the APIs can be brought into an intimate physical admixture with one or more pharmaceutical carriers according to conventional pharmaceutical formulating techniques. The carrier(s) may take a wide variety of forms depending on the desired form for administration, e.g., oral or pulmonary (including nasal and buccal), preferably buccal inhalation.

In preparing the pharmaceutical formulations in their dosage forms for administration, any of the usual pharmaceutical excipients may be employed, such as, for example, diluents of a solid or liquid nature, flavouring agents, preservatives, colouring agents, and the like.

Formulations according to any aspect of the invention will preferably contain at least about 0.1% of the API(s). The percentage of the API(s) in these formulations/compositions may, of course, be varied and may conveniently be between about 2% to about 60% by weight of the unit dose. The amount of the API(s) in such therapeutically useful compositions is such that an effective dosage (i.e. the therapeutically effective amount) will be obtained.

Methods of Preparation

In another aspect of the present invention, there is provided a process for preparing an amorphous form of vilanterol trifenatate as defined herein, the method comprising:

(a) providing of a solution comprising vilanterol trifenatate; and (b) isolating the amorphous form of vilanterol trifenatate by spray drying the solution.

Any suitable solvent may be used to provide a solution comprising vilanterol trifenatate. The solvent may or may not contain water, i.e. the solvent may be 'dry' or 'wet'. For example, the solvent may contain some trace amounts/residual water from the preparation thereof. Optionally, additional water may or may not be added to the solvent. Measures may be taken to avoid contact of the preparation ingredients with water. The solvent may be non-aqueous or substantially free from water. For optimal results, spray drying should, preferably, be conducted with a solvent having a boiling point below about 120° C.

It will be appreciated those persons skilled in the art of spray drying that the particular physical properties of the solution/solvent(s) fed into the spray drying apparatus should be selected depending on the nature and condition of the drying fluid and the desired result.

Suitable solvents for use in the invention include, but are not limited to, any one or more of: alcohols, acetonitrile, anisole, butyl acetate, dichloromethane, 1,4-dioxane, 1,2-dimethoxyethane, ethyl formate, ethyl acetate, isobutyl acetate, isopropyl acetate, methyl tetrahydrofuran, nitromethane, propyl acetate, p-xylene, tetrahydrofuran and toluene. Preferably, the solvent is methanol or ethanol.

The solution comprising the vilanterol trifenatate may be formed in any way, using conventional methods known in the art for the preparation of a solution. For example, crystalline vilanterol trifenatate may, be dissolved in a suitable solvent. Typical methods known in the art to facilitate or cause dissolution, such as stirring and heating, may be applied to provide a homogenous or substantially homogenous solution of the vilanterol trifenatate. Any suitable temperature may be used to facilitate dissolution of the solid and provide a homogeneous solution. Ideally, the solvent may be heated to any temperature below its boiling point, which is preferably below 120° C. and more preferably below about 100° C., especially below about 80° C., such as below 60° C. Dissolution may be aided by constant or intermittent stirring as required.

As will be appreciated by those persons skilled in the art, the particular concentrations of a solution to be spray dried will depend on various factors, such as the nature and condition of the drying fluid, the degree of solubility of the solute in the solvent, and the desired result. Those skilled in the art have the experience and know-how to determine, as a matter of routine experimentation, a suitable concentration for the solution comprising vilanterol trifenatate to provide the desired result from spray drying.

Where suitable, the solution comprising vilanterol trifenatate may have a concentration of up to about 30% weight/weight (w/w) of vilanterol trifenatate in the solvent. Preferably, the concentration of the vilanterol trifenatate is at least about 0.1 wt. % of the solution.

In accordance with the process for preparing the amorphous form of vilanterol trifenatate, described herein, such a process may, preferably, comprise:

suspending vilanterol trifenatate in ethanol, preferably wherein at least 35 times the volume of solvent is used relative to the weight of the solid (i.e. 1 g of solid to at least 35 ml of solvent); heating the suspension, preferably up to 50° C., and isolating the amorphous form by spray drying the solution.

In accordance with the process for preparing the amorphous form of vilanterol trifenatate, described herein, such a process may comprise:

dissolving vilanterol trifenatate in methanol, preferably wherein at least 38 times the volume of solvent is used relative to the weight of the solid (i.e. 1 g of solid to at least 38 ml of solvent), and preferably at 25° C., optionally stirring the solution at preferably 25° C.; and isolating the amorphous form, preferably by spray drying the solution.

The process of the present invention may optionally further comprise micronizing the amorphous vilanterol trifenatate thus prepared to obtain particles having with a particle size suitable for inhalation.

The process of the invention, may optionally further comprise characterisation of the amorphous form of vilanterol trifenatate thus prepared as described herein above, for example by a method including: obtaining an X-ray powder diffraction (XRPD) pattern using copper K-alpha1 radiation, as depicted in FIG. 1; and/or obtaining one or more of:

a differential scanning calorimetry profile having a glass transition (Tg) event at 32° C. and a degradation event with an onset at 189° C. and a peak at 191° C., wherein the differential scanning calorimetry measurement is performed in accordance with the methods and parameters described herein a thermogravimetric analysis (TGA) profile having a weight loss of less than about 0.5%, preferably less than about 0.4%, and more preferably 0.35% or less, as depicted in FIG. 3, wherein the thermogravimetric analysis is performed in accordance with the methods and parameters described herein dynamic vapour sorption (DVS) analysis showing a mass increase of less than about 2% at 80% RH at 25° C., preferably less than about 1.5% at 80% RH at 25° C., and most preferably less than about 1.4% at 80% RH at 25° C., wherein the dynamic vapour sorption analysis is performed in accordance with the methods and parameters described herein as slightly hygroscopic based on results obtained from kinetic moisture sorption measurements obtained by dynamic vapour sorption analysis, and determining a % weight change using the following equation:

(1) % weight change=$[(W_2-W_1)/W_1]*100$, wherein $W_1$ is the weight of the sample at the start of the experiment at 25° C. and 40% RH and $W_2$ is the weight of the sample at 25° C. and 80% RH in the first absorption cycle, and wherein, in accordance with the classifications of the version 7 of the European Pharmacopeia, a calculated weight change of 0.2-2% is indicative of a slightly hygroscopic substance XRPD patterns that are the same or substantially the same following exposure of the amorphous form of vilanterol trifenatate to conditions of 60% RH at 25° C. for 7 days Accordingly, an amorphous form of vilanterol trifenatate obtained or obtainable according to the processes described herein, may be used or prepared for use in a pharmaceutical formulation, which is preferably for treatment of respiratory diseases, such as asthma or a chronic obstructive pulmonary disease.

EXAMPLES

The following examples are provided to illustrate the amorphous compound of the present invention, the process of the present invention, and for comparison of against the prior art; such examples are not intended to be construed as limitations of the present invention—minor variations may be resorted to without departing from the scope of the present invention.

Comparative Example 1: Preparation of Alleged 'Amorphous' Form in Research Disclosure Using Hot Filtration A supersaturated slurry was prepared by stirring 6.0 g of crystalline vilanterol trifenatate of Form I in 2.5 mL of a solvent mixture of 50:50 toluene: methanol at 60° C. for 1.5 hours, followed by filtering the slurries at that temperature and cooling gradually for 48 hours to afford solids, which were dried under vacuum of 200 mbar for 24 h.

Figure 6A:
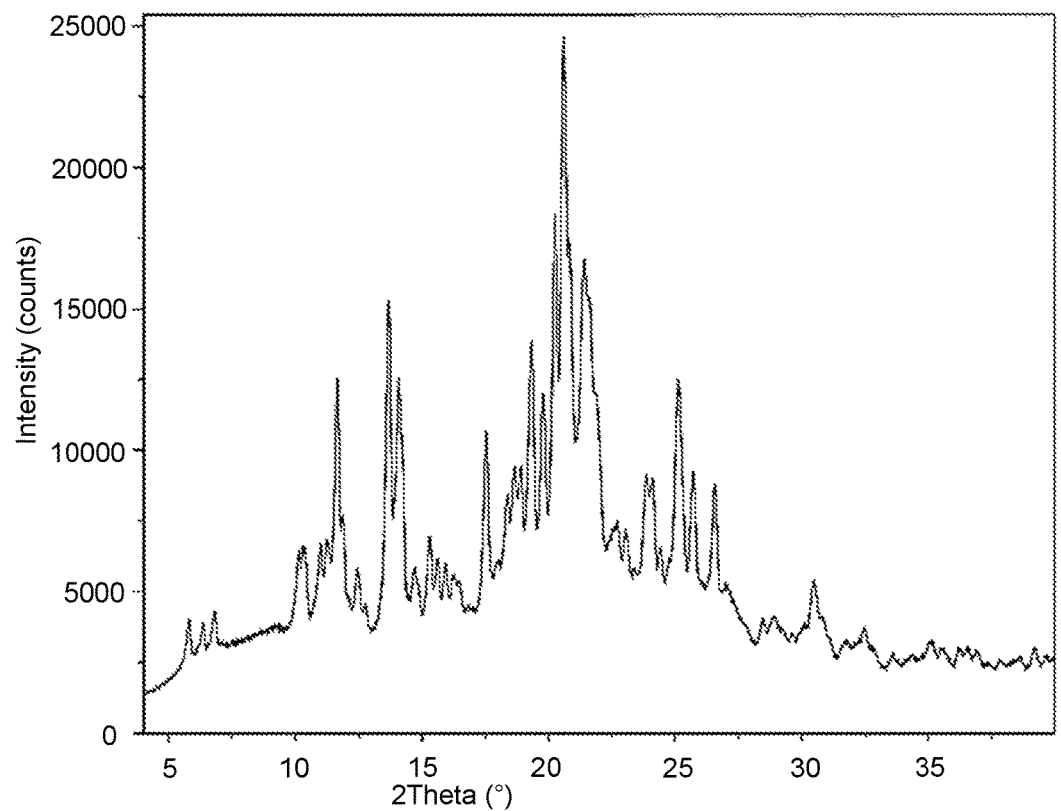
FIG. 6a: XRPD pattern of the solid obtained following 'hot filtration' experimental method described in the Research Disclosure.
Figure 6B:
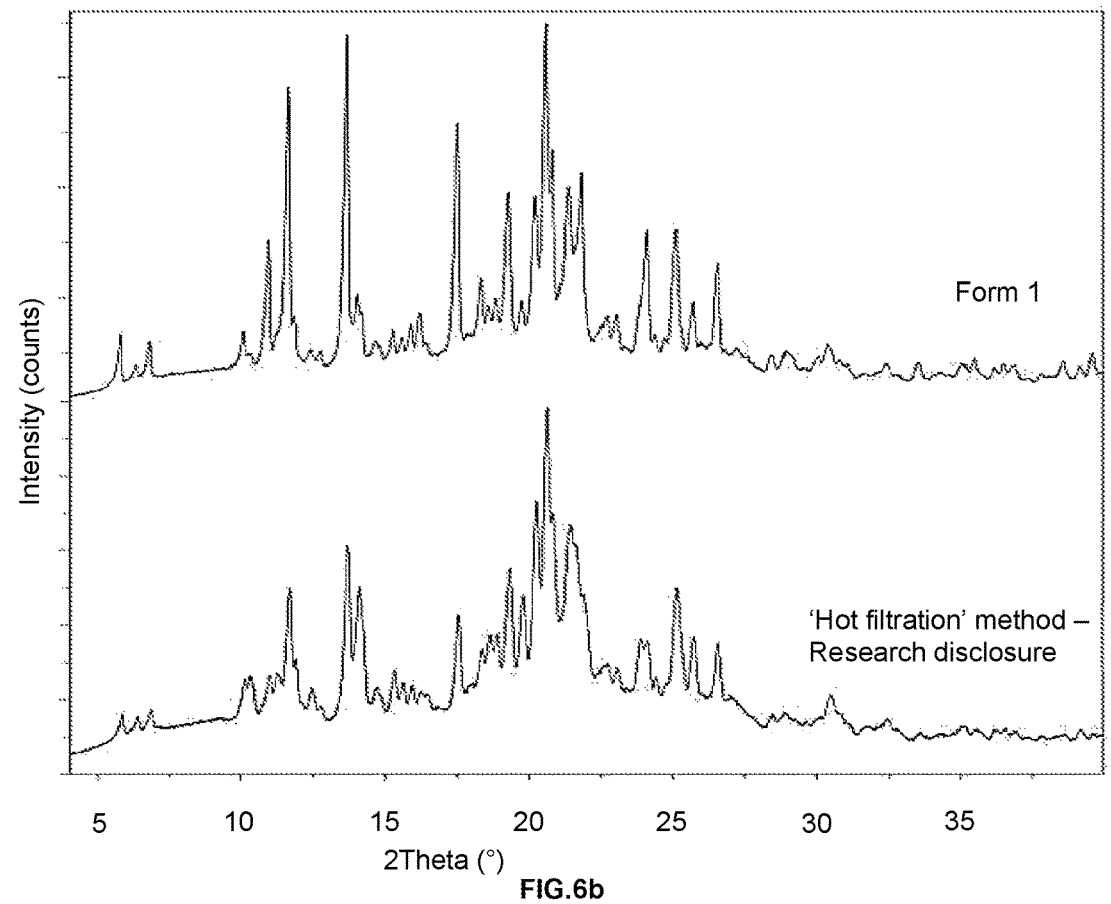
FIG. 6b: XRPD pattern overlay of the solid obtained following 'hot filtration' experimental method described in the Research Disclosure and Form 1.
Figure 7:
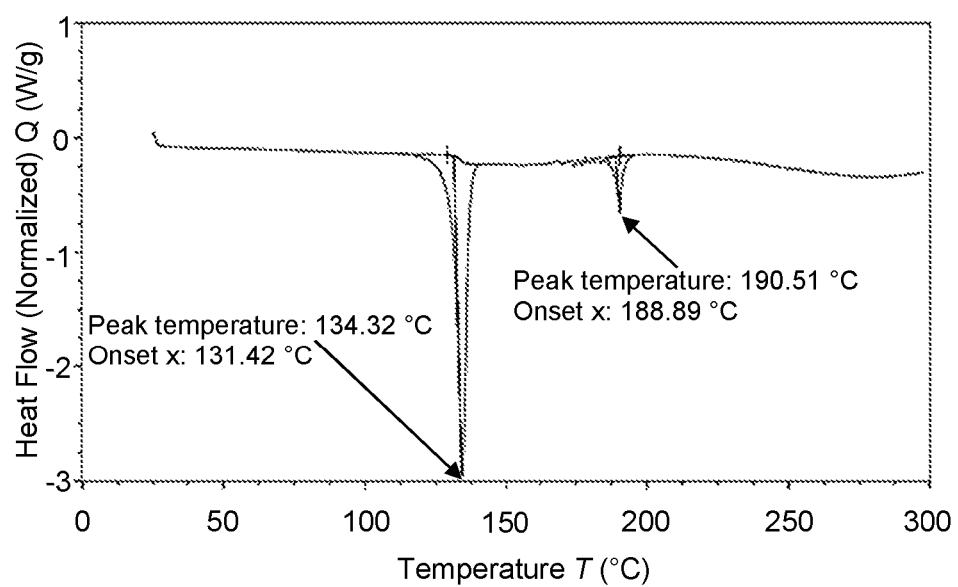
FIG. 7: DSC of the solid obtained following 'hot filtration' experimental method described in the Research Disclosure.

The solid was characterized by DSC and XRPD analysis and the results are presented in FIGS. 6 and 7. The results reveal the presence of a crystalline form identical to crystalline Form I (FIG. 6b).

Example 2—Preparation of Amorphous Form of Vilanterol Trifenatate 20 g of vilanterol trifenatate form I is suspended in 700 mL of absolute ethanol and the suspension heated up to 50° C. The clear solution is stirred for 1 h at a temperature up to 50° C. and fed into a spray dryer. N150: N2: 0.4 bar; Rot: 50 mm; Tout: 35° C.; Tin: 50° C.; PP25%. The amorphous form is isolated. Yield: 11.9 g (59% w/w).

Example 3: Preparation of Amorphous Form of Vilanterol Trifenatate 10 g of vilanterol trifenatate form I are dissolved in 380 mL of methanol. The clear solution is stirred for 1 h at a temperature up to 25° C. and fed into a spray dryer. N150: N2: 0.4 bar; Rot: 40 mm; Tout: 28° C.; Tin: 44° C.; PP25%. The amorphous form is isolated. Yield: 7.4 g (74% w/w).

In the examples and methods of processes of the present invention, the following protocols were followed:
Instrument Parameters and Protocols
HPLC—High Performance Liquid Chromatography
HPLC analysis was conducted using a waters system under the following conditions:
Column: waters symmetry shield rp18 4.6×150 mm 3.5 micra
Flow rate: 0.8 ml/min
Injection volume: 10 ul
Temperature: 30° c.
Solvents a: h2o (0.1% tfa)
Solvent b: ch3cn
The gradient elution method as follows:

| Time (min.) | Flow (ml/min.) | Mobile phase a (%) | Mobile phase b (%) |
|---|---|---|---|
| 0.01 | 0.80 | 85.0 | 15.0 |
| 0.10 | 0.80 | 85.0 | 15.0 |
| 36.00 | 0.80 | 20.0 | 80.0 |
| 42.00 | 0.80 | 20.0 | 80.0 |
| 42.10 | 0.80 | 85.0 | 15.0 |
| 50.00 | 0.80 | 85.0 | 15.0 |

XRPD—The X-Ray Powder Diffraction

X-ray powder patterns were recorded using the PANalytical X'Pert PRO X-ray diffraction system equipped with a PW3373/00 Cu LFF DK184511 X-Ray tube and a X'Celerator RTMS (Real Time Multiple Strip) detector under the following conditions:

| Measurement details | |
|---|---|
| Measurement type: | Single Scan |
| Sample mode | Reflection |
| Voltage (kV): | 40 |
| Current (mA): | 40 |
| Sample Movement mode | Spinning |
| Rotation time (s): | 1.0 |
| Scan | |
| Scan axis: | Gonio |
| Scan mode: | Continuous |
| Scan range: | 3.0010-39.9997 |
| Step size (°): | 0.0167 |
| Counting time (s): | 12.700 |
| N° of points: | 2214 |
| Used wavelength | |
| Intended wavelength type: | Kα1 |
| Kα1 (A): | 1,540598 |
| Kα2 (A): | 1,544426 |
| Kα2/Kα1 intensity ratio: | 0,50 |
| Kα (A): | 1,541874 |
| Kα (A): | 1,392250 |
| Incident beam path | |
| Radius (mm): | 240,0 |
| Soller slit | 0.04 rad |
| Mask | 15 mm |
| Divergent slit | 1/4° |
| Anti-scatter slit | 1/2° |
| Diffracted beam path | |
| Anti-scatter slit | 5.0 mm |
| Filter | Nickel |
| Soller slit | 0.04 rad |
| Detector | X'Celerator |
| Mode | Scanning |
| Active length (2Theta) | 2.122° |

DSC—Differential Scanning Calorimetry

The analysis was carried out using a DSC Q200 TA instruments equipped with a refrigerator cooling system (RCS40) and autosampler. The sample was weighed in an aluminum hermetic pan with pinhole. The analysis was performed heating the sample from 25° C. to 350° C. at 10° C./min.

TGA—Thermogravimetric Analysis

The analysis was carried out using the Mettler Toledo TGA/DSC1. The sample was weighed in an aluminum pan hermetically sealed with an aluminum pierced cover. The analysis was performed heating the sample from 25° C. to 320° C. at 10° C./min.

TGA-FTIR coupled with Thermo Nicoled is 10 spectometer. The analysis of FIG. 3 was carried out using a thermogravimetric analyser Q500 (TA Instruments). The sample was placed in a platinum sample pan and the analysis was performed heating the sample from room temperature to 350° C. at 10° C./min. DVS—Dynamic thermogravimetric analysis The sample was subjected to DVS measuring using SMS-DVS intrinsic. The kinetic moisture sorption measurement was performed at 25° C. and in a RH % range described in the following:
From 40% RH to 90% RH
Form 90% RH to 0% RH From 0% RH to 90% RH
From 90% RH to 0% RH The sample was analyzed by XRPD after the analysis.

Hygroscopicity

The hygroscopicity of the sample was determined using the method reported in the academic article "Efficient throughput method for hygroscopicity classification of an active and inactive pharmaceutical ingredients by water vapor sorption analysis" V. Murikipudi et al., Pharmaceutical Development and Technology, 2013, 18(2): 348-358.

The hygroscopicity was calculated using the following equation:

$$\% \text{ Weight Change} = [(W_2 - W_1)/W_1] * 100, \quad (1)$$

wherein $W_1$ is the weight of the sample at the start of the experiment (25° C. and 40% RH), and $W_2$ is the weight of the sample at 25° C. and 80% RH in the first absorption cycle.

| Ph.Eur. 7.0 CLASSIFICATION | CRITERIA |
|---|---|
| Non hygroscopic | Increase in mass is less than 0.2% |
| Slightly hygroscopic | Increase in mass is less than 2% and equal to or greater than 0.2% |
| Hygroscopic | Increase in mass is less than 15% and equal to or greater than 2% |
| Very Hygroscopic | Increase in mass is equal to or greater than 15% |
| Deliquescent | Sufficient water is absorbed to form a liquid |

The invention claimed is:

1. An amorphous form of vilanterol trifenatate, characterised by the X-ray powder diffraction (XRPD) pattern, obtained using copper K-alpha1 radiation, depicted in FIG. 1.

2. The amorphous form of vilanterol trifenatate obtained by spray drying a solution comprising vilanterol trifenatate, wherein the amorphous form is characterised by the X-ray powder diffraction (XRPD) pattern, obtained using copper K-alpha1 radiation, depicted in FIG. 1.3.

3. The amorphous form of vilanterol trifenatate according to claim 1, further characterised by a differential scanning calorimetry profile having a glass transition (Tg) event with an onset of 32° C. and a degradation event with a onset at 189° C. and a peak at 191° C., optionally wherein the sample is weighed in an aluminium hermetic pan with pinhole and the analysis performed by heating the sample from 25° C. to 350° C. at 10° C./min.

4. The amorphous form of vilanterol trifenatate according to claim 1, further characterised by a thermogravimetric analysis (TGA) profile having a weight loss of less than about 0.5% as depicted in FIG. 3, optionally wherein the sample is weighed in a platinum sample pan and the analysis was performed by heating the sample from room temperature to 350° C. at 10° C./min.

5. The amorphous form of vilanterol trifenatate according to claim 1, further characterised by a dynamic vapour sorption analysis having a mass increase of less than about 2% at 80% RH at 25° C.

6. The amorphous form of vilanterol trifenatate according to claim 1, further characterised by an XRPD pattern that is the same as that depicted in FIG. 1, following exposure of the amorphous form of vilanterol trifenatate to conditions of 60% RH at 25° C. for 7 days.

7. The amorphous form of vilanterol trifenatate according to claim 1, for use in treating respiratory diseases, wherein treating the respiratory disease comprises administration of the amorphous form of vilanterol trifenatate to a patient in need thereof.

8. The amorphous form of vilanterol trifenatate according to claim 1 wherein the amorphous form of vilanterol trifenatate is comprised in a pharmaceutical formulation together with a pharmaceutically acceptable carrier, optionally wherein the pharmaceutical formulation is suitable for administration by inhalation.

9. The amorphous form of vilanterol trifenatate according to claim 8 wherein the pharmaceutical formulation further comprises one or more additional active pharmaceutical ingredient(s).

10. A process for the preparation of the amorphous form of vilanterol trifenatate according to claim 1, the process comprising:
(a) providing of a solution comprising vilanterol trifenatate; and
(b) isolating the amorphous form of vilanterol trifenatate by spray drying the solution.

11. The process for the preparation of the amorphous form of vilanterol trifenatate according to claim 10, wherein providing a solution comprising vilanterol trifenatate comprises dissolving crystalline vilanterol trifenatate in a solvent.

12. The process according to claim 11, wherein the solvent is one or more solvents selected from the group consisting of acetonitrile, anisole, butyl acetate, dichloromethane, 1,4-dioxane, 1,2-dimethoxyethane, ethyl formate, ethyl acetate, isobutyl acetate, isopropyl acetate, methyl tetrahydrofuran, nitromethane, propyl acetate, p-xylene, tetrahydrofuran, toluene and alcohols.

13. The process according to claim 10, wherein the process further comprises micronization of the amorphous form of vilanterol trifenatate, optionally wherein the micronization step is adapted to produce a particle size distribution of Dv90 of less than about 12 μm.

14. A pharmaceutical formulation comprising an amorphous form of vilanterol trifenatate characterised by the XRPD pattern, obtained using copper K-alpha1 radiation, depicted in FIG. 1, and optionally a pharmaceutically acceptable carrier therefor.

15. The amorphous form of vilanterol trifenatate for use in treating respiratory diseases according to claim 7, wherein the amorphous form of vilanterol trifenatate is comprised in a pharmaceutical formulation together with a pharmaceutically acceptable carrier, optionally wherein the pharmaceutical formulation is suitable for administration by inhalation.

16. The amorphous form of vilanterol trifenatate for use in treating respiratory diseases according to claim 15, wherein the pharmaceutical formulation further comprises one or more additional active pharmaceutical ingredient(s).

17. The amorphous form of vilanterol trifenatate for use in treating respiratory diseases according to claim 7, wherein the respiratory diseases comprise asthma or a chronic obstructive pulmonary disease.

18. The amorphous form of vilanterol trifenatate for use in treating respiratory diseases according to claim 15, wherein the respiratory diseases comprise asthma or a chronic obstructive pulmonary disease.

19. The amorphous form of vilanterol trifenatate for use in treating respiratory diseases according to claim 16, wherein the respiratory diseases comprise asthma or a chronic obstructive pulmonary disease.

* * * * *